(12) United States Patent
Dahl et al.

(10) Patent No.: US 8,017,631 B2
(45) Date of Patent: Sep. 13, 2011

(54) OXADIAZOLE DERIVATIVES AND THEIR MEDICAL USE

(75) Inventors: Bjarne H. Dahl, Lynge (DK); Dan Peters, Malmö (SE); Gunnar M. Olsen, Smørum (DK); Daniel B. Timmermann, Herlev (DK); Susanne Jørgensen, Frederiksberg (DK)

(73) Assignee: Neurosearch A/S, Ballerup (DK)

( * ) Notice: Subject to any disclaimer, the term of this patent is extended or adjusted under 35 U.S.C. 154(b) by 946 days.

(21) Appl. No.: 11/919,146

(22) PCT Filed: Apr. 24, 2006

(86) PCT No.: PCT/EP2006/061773
§ 371 (c)(1),
(2), (4) Date: Oct. 24, 2007

(87) PCT Pub. No.: WO2006/114400
PCT Pub. Date: Nov. 2, 2006

(65) Prior Publication Data
US 2009/0312347 A1  Dec. 17, 2009

Related U.S. Application Data

(60) Provisional application No. 60/674,711, filed on Apr. 26, 2005.

(30) Foreign Application Priority Data

Apr. 26, 2005  (DK) .................................. 2005 00612

(51) Int. Cl.
A61K 31/4245 (2006.01)
C07D 413/04 (2006.01)

(52) U.S. Cl. ..................................... 514/340; 546/269.1

(58) Field of Classification Search .............. 546/269.1; 514/340
See application file for complete search history.

(56) References Cited

U.S. PATENT DOCUMENTS

| | | | |
|---|---|---|---|
| 3,211,742 A | 10/1965 | Lenaers | |
| 3,574,842 A | 4/1971 | Bauer et al. | |
| 3,647,809 A | 3/1972 | Harsanyi et al. | |
| 4,022,901 A * | 5/1977 | Narayanan et al. | 514/340 |
| 4,065,563 A | 12/1977 | Narayanan et al. | |
| 4,203,894 A * | 5/1980 | Kurtz et al. | 534/773 |
| 5,817,679 A | 10/1998 | Shen et al. | |
| 6,060,473 A | 5/2000 | Shen et al. | |
| 6,130,217 A * | 10/2000 | Arnold et al. | 514/253.1 |
| 2003/0055085 A1 | 3/2003 | Wagenen et al. | |
| 2004/0266757 A1 | 12/2004 | Galli et al. | |

FOREIGN PATENT DOCUMENTS

| | | |
|---|---|---|
| FR | 2 451 932 A | 10/1980 |
| WO | WO-02/100826 A | 12/2002 |
| WO | WO-2004/058253 A | 7/2004 |
| WO | WO-2004/072050 A1 | 8/2004 |
| WO | WO-2004/103279 A2 | 12/2004 |
| WO | WO-2004/110351 A | 12/2004 |
| WO | WO-2005/032465 A2 | 4/2005 |
| WO | WO-2005/058848 A1 | 6/2005 |

OTHER PUBLICATIONS

Balant et al., "Metabolic Considerations, etc.," in Manfred ed, Burger's Medicinal Chemistry and Drug Discovery, 5th ed. vol. 1: Principles and Practice, John Wiley & Sons, Inc., 1995.*
Torgova et al., "Influence of Chemical Structure, etc.," Brazilian J of Physics (2002), 32(2B), 593-601.*
Becchi et al., "Dielectric, calorimetric, etc.," CA 137:270916 (2002).*
Lessel et al., "Synthesis of, etc.," CA 132:237033 (2000).*
Clarke, "The synthesis of, etc.," Journal of the Chemical Society (1954) 4251-3.*
CA 421568-76-5, May 24, 2002, Pyridine, 3-[5-(5-nitro-2-furanyl)-1,2,4-oxadiazol-3-yl], XP-002393097.
Poulain et al., "Parallel synthesis of 1,2,4-oxadiazoles from carboxylic acids using an improved, uronium-based, activation", Tetrahedron letters, vol. 42, pp. 1495-1498, 2001.

* cited by examiner

*Primary Examiner* — Patricia Morris
(74) *Attorney, Agent, or Firm* — Birch, Stewart, Kolasch & Birch, LLP

(57) ABSTRACT

This invention relates to novel oxadiazole derivatives, which are found to be modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

2 Claims, No Drawings

OXADIAZOLE DERIVATIVES AND THEIR MEDICAL USE

This application is the National Phase of PCT/EP2006/061773 filed on Apr. 24, 2006, which claims priority under 35 U.S.C. 119(e) to U.S. Provisional Application No. 60/674,711 filed on Apr. 26, 2005 and under 35 U.S.C. 119(a) to Patent Application No. PA 2005 00612 filed in Denmark on Apr. 26, 2005. Both of these prior applications are hereby expressly incorporated by reference into the present application.

TECHNICAL FIELD

This invention relates to novel oxadiazole derivatives, which are found to be modulators of the nicotinic acetylcholine receptors. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

Nicotinic acetylcholine receptors (nAChRs) are pentameric ligand gated ion channels and widely distributed throughout the central (CNS) and peripheral (PNS) nervous systems. At least 12 subunit proteins, i.e. $\alpha 2$-$\alpha 10$ and $\beta 2$-$\beta 4$, have been identified in neuronal tissue. These subunits provide for a great variety of homomeric and heteromeric combinations that account for the diverse receptor subtypes. For example, the predominant receptor that is responsible for high affinity binding of nicotine in brain tissue has composition $\alpha 4\beta 2$, while another major population of receptors is comprised of the homomeric $\alpha 7$.

Discovery of the important role played by nAChRs in several CNS disorders has called attention to these membrane proteins and to ligands able to modulate their functions. The existence of different subtypes at multiple levels has complicated the understanding of this receptor's physiological role, but at the same time has increased the efforts to discover selective compounds in order to improve the pharmacological characterization of this kind of receptor and to make safer the possible therapeutic use of its modulators.

SUMMARY OF THE INVENTION

The present invention is devoted to the provision novel modulators of the nicotinic receptors, which modulators are useful for the treatment of diseases or disorders related to the nicotinic acetylcholine receptor (nAChR).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances, in particular nicotine.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides oxadiazole derivatives of Formula I

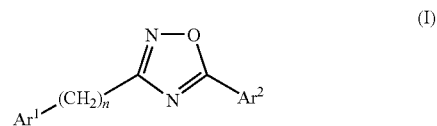

any of its isomers or any mixture of isomers, an N-oxide, a prodrug, or a pharmaceutically-acceptable addition salt thereof, wherein n is 0, 1, 2 or 3;

$Ar^1$ represents an monocyclic carbocyclic or heterocyclic group selected from cycloalkyl, phenyl, thienyl, furanyl, pyridinyl, and pyrazinyl, which monocyclic carbocyclic or heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro and cyano; and $Ar^2$ represents an aromatic monocyclic heterocyclic group selected from phenyl, thienyl, furanyl, pyrrolyl, pyrazolyl, thiazolyl, 1,3,4-thiadiazolyl and pyridinyl which aromatic monocyclic heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro, cyano and amino.

In a second aspect the invention provides pharmaceutical compositions comprising a therapeutically effective amount of the oxadiazole derivative of the invention, or a pharmaceutically-acceptable addition salt thereof, together with at least one pharmaceutically-acceptable carrier or diluent.

Viewed from another aspect the invention relates to the use of the oxadiazole derivative of the invention, or a pharmaceutically-acceptable addition salt thereof, for the manufacture of pharmaceutical compositions/medicaments for the treatment, prevention or alleviation of a disease or a disorder or a condition of a mammal, including a human, which disease, disorder or condition is responsive to modulation of cholinergic receptors.

In yet another aspect the invention provides a method for treatment, prevention or alleviation of diseases, disorders or conditions of a living animal body, including a human, which disorder, disease or condition is responsive to modulation of cholinergic receptors, and which method comprises the step of administering to such a living animal body in need thereof a therapeutically effective amount of the oxadiazole derivative of the invention.

Other objects of the invention will be apparent to the person skilled in the art from the following detailed description and examples.

DETAILED DISCLOSURE OF THE INVENTION

Oxadiazole Derivatives

In its first aspect the invention provides oxadiazole derivatives of Formula I

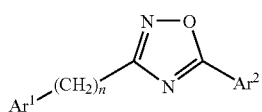

(I)

any of its isomers or any mixture of isomers, an N-oxide, a prodrug, or a pharmaceutically-acceptable addition salt thereof, wherein n is 0, 1, 2 or 3;

$Ar^1$ represents an monocyclic carbocyclic or heterocyclic group selected from cycloalkyl, phenyl, thienyl, furanyl, pyridinyl, and pyrazinyl, which monocyclic carbocyclic or heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro and cyano; and $Ar^2$ represents an aromatic monocyclic heterocyclic group selected from phenyl, thienyl, furanyl, pyrrolyl, pyrazolyl, thiazolyl, 1,3,4-thiadiazolyl and pyridinyl which aromatic monocyclic heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro, cyano and amino.

In a preferred embodiment the oxadiazole derivative of the invention is a compound of Formula I, provided, however, that the compound is not 3-(5-(5-Nitro-furan-2-yl)-[1,2,4]oxadiazol-3-yl)-pyridine; or 3-(5-(3-Nitro-phenyl)-[1,2,4]oxadiazol-3-yl)-pyridine.

In a preferred embodiment the oxadiazole derivative of the invention is a compound of Formula I wherein n is 0, 1, 2 or 3.

In a more preferred embodiment n is 0 or 1.

In an even more preferred embodiment n is 0.

In a still more preferred embodiment n is 1.

In another preferred embodiment the oxadiazole derivative of the invention is a compound of Formula I wherein $Ar^1$ represents an monocyclic carbocyclic or heterocyclic group selected from cycloalkyl, phenyl, thienyl, furanyl, pyridinyl, and pyrazinyl, which monocyclic carbocyclic or heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro and cyano.

In a more preferred embodiment $Ar^1$ represents cycloalkyl, in particular cyclopropyl.

In an even more preferred embodiment $Ar^1$ represents cyclopropyl, cyclobutyl, cyclopentyl, cyclohexyl or cycloheptyl.

In a another preferred embodiment $Ar^1$ represents an aromatic monocyclic carbocyclic or heterocyclic group selected from phenyl, thienyl, furanyl, pyridinyl, and pyrazinyl, which monocyclic carbocyclic or heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro and cyano.

In a more preferred embodiment $Ar^1$ represents an aromatic monocyclic carbocyclic group selected from phenyl and naphthyl, which aromatic monocyclic carbocyclic group is optionally substituted one or more times with substituents selected from the group consisting of alkyl, cycloalkyl, cycloalkyl-alkyl, halo, haloalkyl, hydroxy, alkoxy, haloalkoxy, nitro and cyano.

In an even more preferred embodiment $Ar^1$ represents phenyl, optionally substituted one or two times with substituents selected from the group consisting of alkyl, cycloalkyl, cycloalkyl-alkyl, halo, haloalkyl, hydroxy, alkoxy, haloalkoxy, nitro and cyano.

In a still more preferred embodiment $Ar^1$ represents phenyl, optionally substituted with halo, in particular fluoro or chloro; haloalkyl in particular trifluoromethyl; haloalkoxy, in particular trifluoromethoxy; nitro or cyano In a yet more preferred embodiment $Ar^1$ represents phenyl, optionally substituted with fluoro, chloro or nitro.

In a further more preferred embodiment $Ar^1$ represents phenyl, optionally substituted with chloro.

In a third preferred embodiment $Ar^1$ represents an aromatic monocyclic heterocyclic group selected from thienyl, furanyl, pyridinyl, and pyrazinyl, which monocyclic carbocyclic or heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro and cyano.

In a more preferred embodiment $Ar^1$ represents an aromatic monocyclic heterocyclic group selected from thienyl, furanyl, pyridinyl, and pyrazinyl, which monocyclic carbocyclic or heterocyclic group is optionally substituted one or two times with substituents selected from the group consisting of halo, haloalkyl, haloalkoxy, nitro and cyano.

In an even more preferred embodiment $Ar^1$ represents an aromatic monocyclic heterocyclic group selected from thienyl, in particular thien-2-yl or thien-3-yl; furanyl, in particular furan-2-yl or furan-3-yl; pyridinyl, in particular pyridin-2-yl, pyridin-3-yl or pyridin-4-yl; and pyrazinyl, in particular pyrazin-2-yl.

In a third preferred embodiment the oxadiazole derivative of the invention is a compound of Formula I wherein $Ar^2$ represents an aromatic monocyclic heterocyclic group selected from phenyl, thienyl, furanyl, pyrrolyl, pyrazolyl, thiazolyl, 1,3,4-thiadiazolyl and pyridinyl, which aromatic monocyclic heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro, cyano and amino.

In a more preferred embodiment $Ar^2$ represents an aromatic monocyclic heterocyclic group selected from phenyl, thienyl, furanyl, pyrrolyl, pyrazolyl, thiazolyl, 1,3,4-thiadiazolyl and pyridinyl, which aromatic monocyclic heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro, cyano and amino.

In an even more preferred embodiment $Ar^2$ represents an aromatic monocyclic heterocyclic group selected from phenyl, thienyl, furanyl, pyrrolyl, pyrazolyl, thiazolyl, 1,3,4-thiadiazolyl and pyridinyl, which aromatic monocyclic heterocyclic group is optionally substituted one or two times with substituents selected from the group consisting of alkyl, in particular methyl, ethyl or propyl; cycloalkyl, in particular cyclopropyl; halo, in particular fluoro or chloro; haloalkyl, in particular trifluoromethyl; nitro; cyano and amino.

In a still more preferred embodiment $Ar^2$ represents an aromatic monocyclic heterocyclic group selected from thienyl, furanyl, pyrrolyl, and pyrazolyl, which aromatic monocyclic heterocyclic group is optionally substituted one or more times with substituents selected from the group consisting of alkyl, cycloalkyl, cycloalkylalkyl, halo, haloalkyl, hydroxy, alkoxy, haloalkoxy, nitro and cyano.

In a yet more preferred embodiment $Ar^2$ represents an aromatic monocyclic heterocyclic group selected from furanyl, pyrrolyl, and pyrazolyl, which aromatic monocyclic heterocyclic group is optionally substituted one or two times with substituents selected from the group consisting of alkyl, cycloalkyl, cycloalkyl-alkyl, halo, haloalkyl, hydroxy, alkoxy, haloalkoxy, nitro and cyano.

In a further more preferred embodiment $Ar^2$ represents an aromatic monocyclic heterocyclic group selected from furanyl, pyrrolyl, and pyrazolyl, which aromatic monocyclic heterocyclic group is optionally substituted with alkyl, halo, haloalkyl, hydroxy, alkoxy, haloalkoxy, nitro or cyano.

In a still further more preferred embodiment $Ar^2$ represents an aromatic monocyclic heterocyclic group selected from furanyl, pyrrolyl, and pyrazolyl, which aromatic monocyclic heterocyclic group is optionally substituted with alkyl, in particular methyl; or nitro.

In a still further more preferred embodiment $Ar^2$ represents an aromatic monocyclic heterocyclic group selected from phenyl, thienyl, furanyl, pyrrolyl, pyrazolyl, thiazolyl, 1,3,4-thiadiazolyl and pyridinyl, which aromatic monocyclic heterocyclic group is optionally substituted with alkyl, in particular methyl, ethyl or propyl; halo, in particular fluoro or chloro; haloalkyl, in particular trifluoromethyl; nitro; cyano or amino.

In a still further more preferred embodiment $Ar^2$ represents phenyl, optionally substituted with alkyl, in particular methyl, ethyl or propyl; halo, in particular fluoro or chloro; haloalkyl, in particular trifluoromethyl; nitro; cyano or amino.

In a still further more preferred embodiment $Ar^2$ represents thienyl or furanyl, optionally substituted with alkyl, in particular methyl, ethyl or propyl; halo, in particular fluoro or chloro; haloalkyl, in particular trifluoromethyl; nitro; cyano or amino.

In a still further more preferred embodiment $Ar^2$ represents pyrrolyl or pyrazolyl, optionally substituted with alkyl, in particular methyl, ethyl or propyl; halo, in particular fluoro or chloro; haloalkyl, in particular trifluoromethyl; nitro; cyano or amino.

In a still further more preferred embodiment $Ar^2$ represents thiazolyl or 1,3,4-thiadiazolyl, optionally substituted with alkyl, in particular methyl, ethyl or propyl; halo, in particular fluoro or chloro; haloalkyl, in particular trifluoromethyl; nitro; cyano or amino.

In a still further more preferred embodiment $Ar^2$ represents pyridinyl, optionally substituted with alkyl, in particular methyl, ethyl or propyl; halo, in particular fluoro or chloro; haloalkyl, in particular trifluoromethyl; nitro; cyano or amino.

In a fourth preferred embodiment the oxadiazole derivative of the invention is a compound of Formula I
  n is 0 or 1;
  $Ar^1$ represents cycloalkyl, in particular cyclopropyl; and
  $Ar^2$ represents thienyl, furanyl, pyrrolyl, or pyrazolyl, which aromatic monocyclic heterocyclic group is optionally substituted with alkyl, in particular methyl: halo, in particular fluoro or chloro; haloalkyl, in particular trifluoromethyl; hydroxyl; alkoxy, in particular methoxy or ethoxy; haloalkoxy, in particular trifluoromethoxy; nitro or cyano.

In a fifth preferred embodiment the oxadiazole derivative of the invention is a compound of Formula I wherein
  n is 0 or 1;
  $Ar^1$ phenyl, optionally substituted one or two times with substituents selected from the group consisting of alkyl, cycloalkyl, cycloalkyl-alkyl, halo, haloalkyl, hydroxy, alkoxy, haloalkoxy, nitro or cyano; and
  $Ar^2$ represents thienyl, furanyl, pyridinyl.

In a sixth preferred embodiment the oxadiazole derivative of the invention is a compound of Formula I wherein
  n is 0 or 1;
  $Ar^1$ represents thienyl or furanyl; and
  $Ar^2$ represents thienyl or furanyl, optionally substituted with alkyl, cycloalkyl, cycloalkyl-alkyl, halo, haloalkyl, hydroxy, alkoxy, haloalkoxy, nitro, cyano or amino.

In a seventh preferred embodiment the oxadiazole derivative of the invention is a compound of Formula I wherein
  n is 0 or 1;
  $Ar^1$ represents pyridinyl or pyrazinyl, optionally substituted with substituents selected from the group consisting of alkyl, cycloalkyl, cycloalkyl-alkyl, halo, haloalkyl, hydroxy, alkoxy, haloalkoxy, nitro or cyano; and
  $Ar^2$ represents phenyl, thienyl, furanyl, pyrrolyl, pyrazolyl or thiazolyl, optionally substituted with alkyl, cycloalkyl, cycloalkyl-alkyl, halo, haloalkyl, hydroxy, alkoxy, haloalkoxy, nitro, cyano and amino.

In an eight preferred embodiment the oxadiazole derivative of the invention is a compound of Formula I wherein
  n is 0;
  $Ar^1$ represents cycloalkyl, in particular cyclopropyl; or
  $Ar^1$ represents phenyl, optionally substituted one or two times with substituents selected from the group consisting of alkyl, cycloalkyl, cycloalkyl-alkyl, halo, haloalkyl, hydroxy, alkoxy, haloalkoxy, nitro and cyano; or
  $Ar^1$ represents an aromatic monocyclic heterocyclic group selected from thienyl, furanyl, pyridinyl, and pyrazinyl, which monocyclic carbocyclic or heterocyclic group is optionally substituted one or two times with substituents selected from the group consisting of halo, haloalkyl, haloalkoxy, nitro and cyano; and
  $Ar^2$ represents an aromatic monocyclic heterocyclic group selected from furanyl, pyrrolyl, and pyrazolyl, which aromatic monocyclic heterocyclic group is optionally substituted with alkyl, in particular methyl or ethyl; halo, in particular fluoro or chloro; haloalkyl, in particular trifluoromethyl; hydroxyl; alkoxy, in particular methoxy or ethoxy; haloalkoxy, in particular trifluoromethoxy; nitro or cyano.

In a ninth preferred embodiment the oxadiazole derivative of the invention is a compound of Formula I wherein
  n is 1;
  $Ar^1$ represents an aromatic monocyclic carbocyclic or heterocyclic group selected from phenyl, thienyl, furanyl, pyridinyl, and pyrazinyl, which monocyclic carbocyclic or heterocyclic group is optionally substituted one or more times with substituents selected from the group consisting of alkyl, cycloalkyl, cycloalkyl-alkyl, halo, haloalkyl, hydroxy, alkoxy, haloalkoxy, nitro and cyano; and
  $Ar^2$ represents an aromatic monocyclic heterocyclic group selected from furanyl, pyrrolyl, and pyrazolyl, which aromatic monocyclic heterocyclic group is optionally substituted with alkyl, in particular methyl or ethyl; halo, in particular fluoro or chloro; haloalkyl, in particular trifluoromethyl; hydroxyl; alkoxy, in particular methoxy or ethoxy; haloalkoxy, in particular trifluoromethoxy; nitro or cyano.

In a tenth preferred embodiment the oxadiazole derivative of the invention is a compound of Formula I wherein n is 1;

Ar$^1$ represents phenyl, optionally substituted one or two times with substituents selected from the group consisting of alkyl, cycloalkyl, cycloalkyl-alkyl, halo, haloalkyl, hydroxy, alkoxy, haloalkoxy, nitro and cyano; and Ar$^2$ represents an aromatic monocyclic heterocyclic group selected from furanyl, pyrrolyl, and pyrazolyl, which aromatic monocyclic heterocyclic group is optionally substituted with alkyl, in particular methyl or ethyl; halo, in particular fluoro or chloro; haloalkyl, in particular trifluoromethyl; hydroxyl; alkoxy, in particular methoxy or ethoxy; haloalkoxy, in particular trifluoromethoxy; nitro or cyano.

In a most preferred embodiment the oxadiazole derivative of the invention is

3-Cyclopropyl-5-(5-nitro-furan-2-yl)-[1,2,4]oxadiazole;
5-(5-Nitro-furan-2-yl)-3-phenyl-[1,2,4]oxadiazole;
5-(5-Nitro-furan-2-yl)-3-(4-fluoro)-phenyl-[1,2,4]oxadiazole;
5-(5-Nitro-furan-2-yl)-3-benzyl-[1,2,4]oxadiazole;
5-(5-Nitro-furan-2-yl)-3-thiophen-2-yl-[1,2,4]oxadiazole;
2-(5-(5-Nitro-furan-3-yl)-[1,2,4]oxadiazol-3-yl)-pyridine;
3-(5-(3-Nitro-phenyl)-[1,2,4]oxadiazol-3-yl)-pyridine;
3-(5-Furan-2-yl-[1,2,4]oxadiazol-3-yl)-pyridine;
3-(5-(5-Nitro-furan-3-yl)-[1,2,4]oxadiazol-3-yl)-pyridine;
3-(5-Furan-3-yl-[1,2,4]oxadiazol-3-yl)-pyridine;
3-[5-(1H-Pyrrol-2-yl)-[1,2,4]oxadiazol-3-yl]-pyridine;
4-(5-Furan-2-yl-[1,2,4]oxadiazol-3-yl)-pyridine;
2-[5-(5-Nitro-furan-2-yl)-[1,2,4]oxadiazol-3-yl]-pyrazine;
3-[5-(11-Methyl-1H-pyrrol-2-yl)-[1,2,4]oxadiazol-3-yl]-pyridine;
3-[5-(1H-Pyrazol-4-yl)-[1,2,4]oxadiazol-3-yl]-pyridine;
3-[5-(2-Methyl-thiazol-4-yl)-[1,2,4]oxadiazol-3-yl]-pyridine;
3-[5-(4-Nitro-phenyl)-[1,2,4]oxadiazol-3-yl]-pyridine;
2-[5-(3-Nitro-phenyl)-[1,2,4]oxadiazol-3-yl]-pyridine;
3-(5-Phenyl-[1,2,4]oxadiazol-3-yl)-pyridine;
3-(3-Pyridin-3-yl-[1,2,4]oxadiazol-5-yl)-benzonitrile;
3-[5-(3-Chloro-phenyl)-[1,2,4]oxadiazol-3-yl]-pyridine;
3-Phenyl-5-(thiophen-3-yl)-[1,2,4]oxadiazole;
4-[5-(3-Nitro-phenyl)-[1,2,4]oxadiazol-3-yl]-pyridine;
3-[5-(3-Fluoro-phenyl)-[1,2,4]oxadiazol-3-yl]-pyridine;
2-[5-(3-Nitro-phenyl)-[1,2,4]oxadiazol-3-yl]-pyrazine;
3-Phenyl-5-(thiophen-2-yl)-[1,2,4]oxadiazole;
3-[5-(2-Nitro-phenyl)-[1,2,4]oxadiazol-3-yl]-pyridine;
3-[5-(3-Trifluoromethyl-phenyl)-[1,2,4]oxadiazol-3-yl]-pyridine;
3-[3-(3-Nitro-phenyl)-[1,2,4]oxadiazol-5-yl]-pyridine;
6-(Pyridin-3-yl-[1,2,4]oxadiazol-5-yl)-pyridine-2-carbonitrile;
5-(3-Pyridin-3-yl-[1,2,4]oxadiazol-5-yl)-furan-2-carbonitrile;
5-(3-Pyridin-3-yl-[1.2.4]oxadiazol-5-yl)-thiophene-2-carbonitrile; or
3-(3-Pyridin-3-yl-[1,2,4]oxadiazol-5-yl)-phenylamine;
any of its isomers or any mixture of isomers, or a pharmaceutically-acceptable addition salt-thereof.

Any combination of two or more of the embodiments described herein is considered within the scope of the present invention.

Definition of Substituents

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cycloalkoxy group designates a "cycloalkyl-O—" group, wherein cycloalkyl is as defined above.

In the context of this invention a cyano-alkyl group designates an alkyl group substituted with CN, wherein alkyl is as defined above.

In the context of this invention halo represents fluoro, chloro, bromo or iodo, and haloalkyl group designates an alkyl group as defined herein, which alkyl group is substituted one or more times with halo. Thus a trihalomethyl group represents e.g. a trifluoromethyl group, a trichloromethyl group, and similar trihalo-substituted methyl groups. Preferred haloalkyl groups of the invention include trihalogenmethyl, preferably —$CF_3$.

In the context of this invention a haloalkoxy group designates an alkoxy group as defined herein, which alkoxy group is substituted one or more times with halo. Preferred haloalkoxy groups of the invention include trihalogenmethoxy, preferably —$OCF_3$.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl. The most preferred aryl group of the invention is phenyl.

In the context of this invention a heteroaryl group designates an aromatic mono- or polycyclic heterocyclic group, which holds one or more heteroatoms in its ring structure. Preferred heteroatoms include nitrogen (N), oxygen (O) and sulphur (S).

Pharmaceutically Acceptable Salts

The oxadiazole derivative of the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a compound of the invention include alkali metal salts, such as the sodium salt of a compound of the invention containing a carboxy group.

In the context of this invention the "onium salts" of N-containing compounds may also be contemplated as pharmaceutically acceptable salts. Preferred "onium salts" include the alkyl-onium salts, the cycloalkyl-onium salts, and the cycloalkylalkyl-onium salts. Particularly preferred onium salts of the invention include those created at the N' position according to the following Formula I'

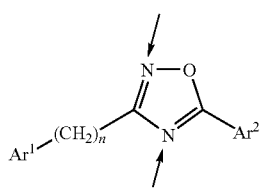

(I)

Isomers

It will be appreciated by those skilled in the art that the compounds of the present invention may exist in different stereoisomeric forms, including enantiomers, diastereomers, as well as geometric isomers (cis-trans isomers). The invention includes all such isomers and any mixtures thereof including racemic mixtures.

Racemic forms can be resolved into the optical antipodes by known methods and techniques. One way of separating the enantiomeric compounds (including enantiomeric intermediates) is by use of an optically active amine, and liberating the diastereomeric, resolved salt by treatment with an acid. Another method for resolving racemates into the optical antipodes is based upon chromatography on an optical active matrix. Racemic compounds of the present invention can thus be resolved into their optical antipodes, e.g., by fractional crystallisation of D- or L-(tartrates, mandelates or camphorsulphonate) salts for example.

Additional methods for the resolving the optical isomers are known in the art. Such methods include those described by Jaques J, Collet A, & Wilen S in "Enantiomers, Racemates, and Resolutions", John Wiley and Sons, New York (1981).

Optical active compounds can also be prepared from optical active starting materials or intermediates.

Methods of Producing Oxadiazole Derivatives

The oxadiazole derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel modulators of the nicotinic receptors, which modulators are useful for the treatment of diseases or disorders related to the nicotinic acetylcholine receptor (nAChR). Preferred compounds of the invention show a positive allosteric modulation of the nicotinic acetylcholine α4β2 receptor subtypes.

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances, in particular nicotine.

In a preferred embodiment the disease, disorder or condition relates to the central nervous system.

The compounds of the invention may also be useful as diagnostic tools or monitoring agents in various diagnostic methods, and in particular for in vivo receptor imaging (neuroimaging), and they may be used in labelled or unlabelled form.

In another preferred embodiment the disease, disorder or condition is a cognitive disorder, learning deficit, memory deficits and dysfunction, Alzheimer's disease, attention deficit, attention deficit hyperactivity disorder (ADHD), Tourette's syndrome, psychosis, depression, bipolar disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, amyotrophic lateral sclerosis (ALS), anxiety, non-OCD anxiety disorders, convulsive disorders, convulsions, epilepsy, neurodegenerative disorders, transient anoxia, induced neurodegeneration, neuropathy, diabetic neuropathy, periferic dyslexia, tardive dyskinesia, hyperkinesia, pain, mild pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhoea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the compounds of the invention are used for the treatment, prevention or alleviation of pain, mild or moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In another more preferred embodiment the compounds of the invention are used for the treatment, prevention or alleviation of smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a third more preferred embodiment the compounds of the invention are used for the treatment, prevention or alleviation of a neurodegenerative disorder, transient anoxia, or induced neuro-degeneration.

In a fourth more preferred embodiment the compounds of the invention are used for the treatment, prevention or alleviation of an inflammatory disorder, inflammatory skin disorder, acne, rosacea, Chron's disease, inflammatory bowel disease, ulcerative colitis, or diarrhoea.

In a fifth more preferred embodiment the compounds of the invention are used for the treatment, prevention or alleviation of diabetic neuropathy, schizophrenia, cognitive or attentional deficits related to schizophrenia, or depression.

In a sixth more preferred embodiment the compounds of the invention are used for the treatment, prevention or alleviation of pain, in particular neuropathic pain, diabetic neuropathy, schizophrenia and cognitive or attentional deficits related to schizophrenia, depression, and for assisting in obtaining smoking cessation.

In a seventh more preferred embodiment the compounds of the invention are used the treatment of withdrawal symptoms caused by termination of use of addictive substances, in particular nicotine containing products such as tobacco, opioids such as heroin, cocaine and morphine, benzodiazepines, benzodiazepine-like drugs, and alcohol.

In an eight more preferred embodiment the compounds of the invention are used for the treatment of anxiety, cognitive disorders, learning deficit, memory deficits and dysfunction, Alzheimer's disease, attention deficit, attention deficit hyperactivity disorder (ADHD), Parkinson's disease, Huntington's disease, Amyotrophic Lateral Sclerosis, Gilles de la Tourette's syndrome, psychosis, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a ninth more preferred embodiment the compounds of the invention are used for the treatment of cognitive disorders, psychosis, schizophrenia and/or depression.

In a tenth more preferred embodiment the compounds of the invention are used for the treatment of diseases, disorders, or conditions associated with smooth muscle contractions, including convulsive disorders, angina pectoris, premature labour, convulsions, diarrhoea, asthma, epilepsy, tardive dyskinesia, hyperkinesia, premature ejaculation, and erectile difficulty.

In an eleventh more preferred embodiment the compounds of the invention are used for the treatment of endocrine disorders, such as thyrotoxicosis, pheochromocytoma, hypertension and arrhythmias.

In a twelfth more preferred embodiment the compounds of the invention are used for the treatment of neurodegenerative disorders, including transient anoxia and induced neuro-degeneration.

In a thirteenth more preferred embodiment the compounds of the invention are used for the treatment of inflammatory diseases, disorders, or conditions, including inflammatory skin disorders such as acne and rosacea, Chron's disease, inflammatory bowel disease, ulcerative colitis, and diarrhoea.

In a fourteenth more preferred embodiment the compounds of the invention are used for the treatment of pain, mild, moderate or severe pain, or pain of acute, chronic or recurrent character, as well as pain caused by migraine, postoperative pain, and phantom limb pain. The pain may in particular be neuropathic pain, chronic headache, central pain, pain related to diabetic neuropathy, to post therapeutic neuralgia, or to peripheral nerve injury.

Finally, in a most preferred embodiment, the compounds of the invention may be useful for the treatment of depression, cognition, dementia, obesity, or associated with withdrawal symptoms caused by nicotine addiction.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

Pharmaceutical Compositions

In another aspect the invention provides novel pharmaceutical compositions comprising a therapeutically effective amount of oxadiazole derivative of the invention.

While a compound of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the oxadiazole derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by the skilled person by use of standard methods and conventional techniques appropriate to the desired formulation. When desired, compositions adapted to give sustained release of the active ingredient may be employed.

In a preferred embodiment, when the pharmaceutical composition of the invention is intended for treating patients with withdrawal symptoms caused by nicotine addiction, formulations such as gums, patches, sprays, inhalers, aerosols, etc., are contemplated.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

The oxadiazole derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of an oxadiazole derivative of the invention.

In the context of this invention the term "treatment" covers treatment, prevention, prophylaxis or alleviation, and the term "disease" covers illnesses, diseases, disorders and conditions related to the disease in question.

The preferred indications contemplated according to the invention are those stated above.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

Examples

The invention is further illustrated with reference to the following examples, which are not intended to be in any way limiting to the scope of the invention as claimed.

EXAMPLES

Preparatory Example

While 3-(5-(5-Nitro-furan-2-yl)-[1,2,4]oxadiazol-3-yl)-pyridine (Compound 1) may be obtained from Ambinter Screening Library, Ambinter, Paris, France, and 3-(5-(3-Nitro-phenyl)-[1,2,4]oxadiazol-3-yl)-pyridine (Compound 2) may be obtained from ComGenex Inc., Budapest, Hungary, the following examples describe the synthesis of a number of compounds representative of the invention.

All reactions involving air sensitive reagents or intermediates were performed under nitrogen and in anhydrous solvents.

Example 1

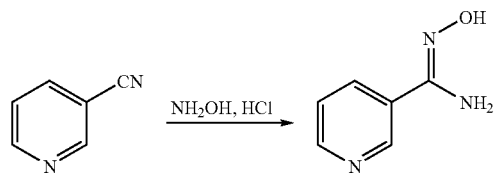

N-Hydroxy-nicotinamidine (Intermediate Compound)

Nicotinonitrile (1 g; 10 mmol) and 1.3 g of hydroxylamine hydrochloride (19 mmol) were dissolved in 15 ml of water. Sodium carbonate (2 g; 24 mmol) in 10 ml of water was continuously added, the resulting solution was stirred and heated at app. 70° C. for 6 hours. Then no more starting material was left (checked by TLC), the reaction mixture was cooled to room temperature, added sodium chloride until saturation and extracted 4 times with 50 ml of ethyl acetate. The organic layer was dried with sodium sulfate and evaporated to a solid. Yield 1 g (76%) of white solid powder.

Similarly was made (Intermediate compounds):
N-Hydroxy-benzamidine;
N-Hydroxy-isonicotinamidine;
4-Fluoro-N-hydroxy-benzamidine;
N-Hydroxy-thiophene-2-carboxamidine;
N-Hydroxy-cyclopropane-carboxamidine;
N-Hydroxy-pyrazine-2-carboxamidine;
N-Hydroxy-2-phenyl-acetamidine;
N-Hydroxy-nicotinamidine;
N-Hydroxy-pyridine-2-carboxamidine; and
N-Hydroxy-3-nitro-benzamidine.

Example 2

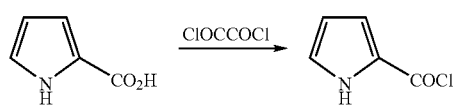

1H-Pyrrole-2-carbonyl-chloride (Intermediate compound)

Oxalyl chloride (6.7 g; 53 mmol) under nitrogen was cooled to 0-5° C., and 0.5 g of Pyrrole-2-carboxylic acid (4 mmol) was added. The reaction mixture was allowed to reach room temperature and heated to 50° C. and stirred at this temperature, until the reaction was finished (controlled by TLC). The reaction mixture was cooled to room temperature and evaporated to an oil, the residue was washed with toluene and dried. The product was used as such in the next reaction.

Similarly was made (Intermediate compounds):
1H-Pyrazole-4-carbonyl chloride;
5-Nitro-furan-2-carbonyl chloride;
2-Methyl-thiazole-4-carbonyl chloride;
Benzoyl chloride;
Thiophene-2-carbonyl chloride;
3-Fluoro-benzoyl chloride;
2-Nitro-benzoyl chloride;
3-Cyano-benzoyl chloride;
4-Nitro-benzoyl chloride;
3-Chloro-benzoyl chloride;
3-Nitro-benzoyl chloride;
Thiophene-2-carbonyl chloride;
5-Bromo-thiophene-2-carbonyl chloride;
5-Bromo-furan-2-carbonyl chloride; and
6-Bromo-pyridine-2-carbonyl chloride.

Example 3

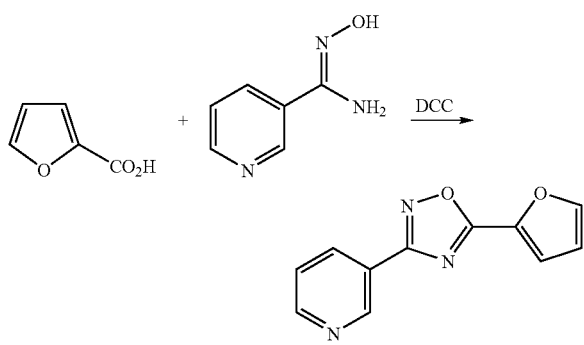

3-(5-Furan-2-yl-[1,2,4]oxadiazol-3-yl)-pyridine
(Compound 3.1)

Furan-2-carboxylic acid (0.8 g; 7 mmol) in 15 ml of dichloromethane was cooled to 0° C., and 0.76 g of 1,3-dicyclohexylcarbodiimide (4 mmol) was added slowly. The reaction mixture was stirred at 0-5° C. for 2 hours and filtered. The filtrate was evaporated, the residue was dissolved in 15 ml of pyridine and added 0.43 g of N-hydroxy-nicotinamidine (3.2 mmol). The reaction mixture was heated at reflux until the reaction was finished (measured by TLC), then cooled to room temperature and poured into 100 ml of water. The precipitate was isolated by filtration and dried under vacuum. The product was isolated by column chromatography. Yield 0.23 g (15%). Mp. 110-114° C.
Similarly was made:

3-(5-Furan-3-yl-[1,2,4]oxadiazol-3-yl)-pyridine
(Compound 3.2); Mp. 105-108° C.

Example 4

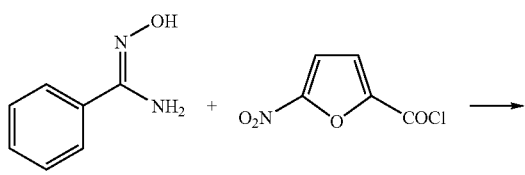

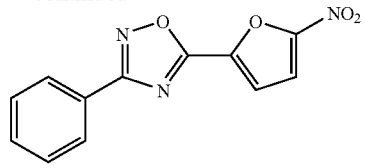

5-(5-Nitro-furan-2-yl)-3-phenyl-[1,2,4]oxadiazole
(Compound 4.1)

N-Hydroxy-benzamidine (0.3 g; 2.1 mmol) was dissolved in 10 ml of dry pyridine and added 0.5 g of 5-nitro-furan-2-carbonyl chloride (2.8 mmol). The reaction mixture was heated at reflux for 3 hours, cooled to room temperature and poured into 50 ml of ice/water, the product precipitated out of solution and was isolated by filtration. Yield 0.3 g (41%) of yellow solid. Mp. 164-166° C.
Similarly was made:
3-[5-(1H-Pyrrol-2-yl)-[1,2,4]oxadiazol-3-yl-pyridine (Compound 4.2); Mp. 200-203° C.;
3-(4-Fluoro-phenyl)-5-(5-nitro-furan-2-yl)-[1,2,4]oxadiazole (Compound 4.3); Mp. 162-164° C.;
3-Benzyl-5-(5-nitro-furan-2-yl)-[1,2,4]oxadiazole (Compound 4.4); Mp. 77-79° C.;
5-(5-Nitro-furan-2-yl)-3-thiophen-2-yl-[1,2,4]oxadiazole (Compound 4.5); Mp. 181-185° C.;
2-{5-(5-Nitro-furan-2-yl)-[1,2,4]oxadiazol-3-yl}-pyridine (Compound 4.6); Mp. 190-191° C.;
2-{5-(5-Nitro-furan-2-yl)-[1,2,4]oxadiazol-3-yl}-pyrazine (Compound 4.7); Mp. 187-189° C.;
3-Cyclopropyl-5-(5-nitro-furan-2-yl)-[1,2,4]oxadiazol (Compound 4.8); Mp. 67-70° C.;
4-{5-(5-Nitro-furan-2-yl)-[1,2,4]oxadiazol-3-yl}-pyridine (Compound 4.9); Mp. 157-160° C.;
3-{5-(1H-Pyrazol-4-yl)-[1,2,4]oxadiazol-3-yl}-pyridine (Compound 4.10); Mp. 219-221° C.;
3-[5-(2-Methyl-thiazol-4-yl)-[1,2,4]oxadiazol-3-yl]-pyridine (Compound 4.11); Mp. 152-154° C.;
3-[5-(4-Nitro-phenyl)-[1,2,4]oxadiazol-3-yl]-pyridine (Compound 4.12); Mp. 179-181° C.;
2-[5-(3-Nitro-phenyl)-[1,2,4]oxadiazol-3-yl]-pyridine (Compound 4.13); 170-171° C.;
3-(5-Phenyl-[1,2,4]oxadiazol-3-yl)-pyridine (Compound 4.14); Mp. 142-143° C.;
3-(3-Pyridin-3-yl-[1,2,4]oxadiazol-5-yl)-benzonitrile (Compound 4.15); Mp. 154-156° C.;
3-[5-(3-Chloro-phenyl)-[1,2,4]oxadiazol-3-yl]-pyridine (Compound 4.16); Mp. 122-123° C.;
3-Phenyl-5-(thiophen-3-yl)-[1,2,4]oxadiazole (Compound 4.17); Mp. Mp. 107-109° C.;
4-[5-(3-Nitro-phenyl)-[1,2,4]oxadiazol-3-yl]-pyridine (Compound 4.18); Mp. 151-153° C.;
3-[5-(3-Fluoro-phenyl)-[1,2,4]oxadiazol-3-yl]-pyridine (Compound 4.19); Mp. 112-113° C.;
2-[5-(3-Nitro-phenyl)-[1,2,4]oxadiazol-3-yl]-pyrazine (Compound 4.20); Mp. 180-182° C.;
3-Phenyl-5-(thiophen-2-yl)-[1,2,4]oxadiazole (Compound 4.21); Mp. 107-109° C.;
3-[5-(2-Nitro-phenyl)-[1,2,4]oxadiazol-3-yl]-pyridine (Compound 4.22); Mp. 104-105° C.;
3-[5-(3-Trifluoromethyl-phenyl)-[1,2,4]oxadiazol-3-yl]-pyridine (Compound 4.23); Mp. 78-83° C.;
3-[3-(3-Nitro-phenyl)-[1,2,4]oxadiazol-5-yl]-pyridine (Compound 4.24); Mp. 173-175° C.;

N-[3-(3-Pyridin-3-yl-[1,2,4]oxadiazol-5-yl)-phenyl]-acetamide (Intermediate);

2-Bromo-6-(3-pyridin-3-yl-[1,2,4]oxadiazol-5-yl)-pyridine (Intermediate);

3-[5-(5-Bromo-furan-2-yl)-[1,2,4]oxadiazol-3-yl]-pyridine (Intermediate); and

3-[5-(5-Bromo-thiophen-2-yl)-[1,2,4]oxadiazol-3-yl]-pyridine (Intermediate).

Example 5

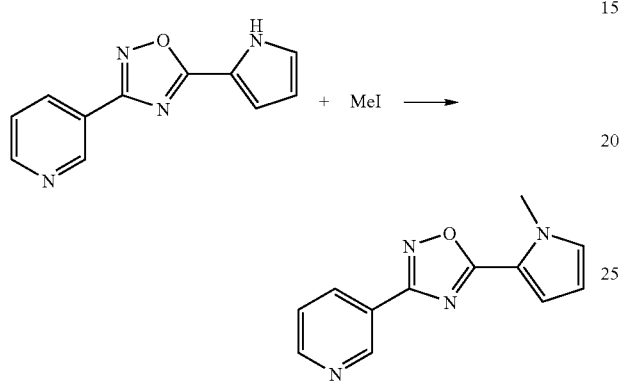

3-{5-(1-Methyl-1H-pyrrol-2-yl)-[1,2,4]oxadiazol-3-yl}-pyridine (Compound 5.1)

3-{5-(1H-pyrrol-2-yl)-[1,2,4]oxadiazol-3-yl}-pyridine (1 g; 0.5 mmol) in 15 ml of dry THF at −70° C. was added 0.18 g of sodium hexamethyl disilazide (1 mmol), the reaction mixture was stirred at −70° C. for 30 min. and at 0° C. for 1 hour. The reaction mixture was cooled to −70° C. and added 0.076 g of iodomethane (0.52 mmol). The reaction mixture was stirred at −70° C. for ½ hour, then at room temperature overnight. The product was isolated by column chromatography. Yield 0.04 g of yellow solid (37%). Mp. 108-109° C.

Example 6

6-(Pyridin-3-yl-[1,2,4]oxadiazol-5-yl)-pyridine-2-carbonitrile (Compound 6.1)

2-Bromo-6-(3-pyridin-3-yl-[1,2,4]oxadiazol-5-yl)-pyridine (250 mg, 0.83 mmol) and 80 mg of potassium cyanide (1.24 mmol) in 15 ml of acetonitrile was degassed three times (vacuum/nitrogene), added a solution of 24 μl Tributyltin chloride (1 μmol) in heptane, 2.3 mg of bis-(diphenylphosphino)ferrocene (4.1 μmol) and 4 mg of bispalladium tris (dibenzylidene acetone) (4.1 μmol) were added. The suspension was degassed three times and stirred at ambident temperature for 30 minutes. The mixture was degassed again and heated at 80° C. for 17 hours. The reaction mixture concentrated, residue was diluted with ethyl acetate and washed with water. The organic layer was dried with sodium sulphate, concentrated, and purified by column chromatography over silica gel using 20% ethyl acetate in petroleum ether, Yield 80 mg. Mp 201-203° C.

Similarly was made:
5-(3-Pyridin-3-yl-[1,2,4]oxadiazol-5-yl)-furan-2-carbonitrile (Compound 6.2) Mp. 141-144° C. and
5-(3-Pyridine-3-yl-[1.2.4]oxadiazol-5-yl)-thiophene-2-carbonitrile (Compound 6.3) Mp. 159-161° C.

Example 7

3-(3-Pyridin-3-yl-[1,2,4]oxadiazol-5-yl)-phenylamine (Compound 7.1)

To a saturated solution of hydrogen chloride in ethanol (20 ml) at 0° C., was added 0.48 g of N-[3-pyridin-3-yl[1,2,4]oxadiazol-5-yl)-phenyl]-acetamide (1.7 mmol) portion wise, after addition, the reaction mixture was allowed to reach room temperature and heated at 50° C. for 15 hours. The reaction mixture was evaporated to an oil and added water. The mixture was added saturated sodium bicarbonate (aq.) and extracted with ethyl acetate, the organic phase was washed with brine, dried with sodium sulphate and evaporated to an oil. The product was isolated by column chromatography. Yield 0.2 g (48%). Mp. 161-163° C.

Example 8

Characterization of hα4β2 Positive Allosteric Modulators Using FLIPR

This experiment shows the ability of a compound representative of the invention (3-(5-(5-Nitro-furan-2-yl)-[1,2,4]oxadiazol-3-yl)-pyridine; Compound 1) to positively modulate the response induced by a sub-maximal concentration of nicotine ($EC_{20\text{-}30}$) in human HEK cells expressing the human nicotinic acetylcholine receptor subtype α4β2. The ability is determined relative to a maximal nicotine response (normally 100 μM). The activity is determined as a standard assay using a fluorometric method in a Fluorescent Image Plate Reader (FLIPR) as described below in more detail.

Full concentration/response curves are generated and $EC_{50}$ values are calculated based on peak values. $EC_{50}$ values (Effective Concentration) represent the concentration of the test substance, at which the nicotine-induced $EC_{20\text{-}30}$ response is positively modulated such that the size of the response equals 50% of a maximal nicotine control response. The maximal positively modulated response is determined relative to the reference (nicotine) response.

The results of this experiment are presented in Table 1 below.

TABLE 1

FLIPR nAChR α4β2 Positive Allosteric Modulator Activity

| Compound | $EC_{50}$ (μM) | Max. Response rel. to Nicotine (%) |
| --- | --- | --- |
| Compound 1 | 6.8 | 97 |

The invention claimed is:
1. An oxadiazole derivative, which is
3-(3-Pyridin-3-yl-[1,2,4]oxadiazol-5-yl)-benzonitrile,
or a pharmaceutically-acceptable addition salt thereof.
2. A pharmaceutical composition comprising a therapeutically effective amount of the oxadiazole derivative of claim 1, or a pharmaceutically-acceptable addition salt thereof, together with at least one pharmaceutically-acceptable carrier or diluent.

* * * * *